United States Patent
Ito et al.

(10) Patent No.: US 10,947,194 B2
(45) Date of Patent: Mar. 16, 2021

(54) METHOD FOR PRODUCING DIHYDROXYINDOLES

(71) Applicant: KAO CORPORATION, Tokyo (JP)

(72) Inventors: Norihiro Ito, Wakayama (JP); Masayoshi Nakamoto, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/760,796

(22) PCT Filed: Oct. 31, 2018

(86) PCT No.: PCT/JP2018/040457
§ 371 (c)(1),
(2) Date: Apr. 30, 2020

(87) PCT Pub. No.: WO2019/088151
PCT Pub. Date: May 9, 2019

(65) Prior Publication Data
US 2020/0339510 A1    Oct. 29, 2020

(30) Foreign Application Priority Data

Nov. 1, 2017   (JP) ............................. JP2017-212035

(51) Int. Cl.
*C07D 209/08*   (2006.01)
(52) U.S. Cl.
CPC ................... *C07D 209/08* (2013.01)
(58) Field of Classification Search
CPC .................................................. C07D 209/08
See application file for complete search history.

(56) References Cited

U.S. PATENT DOCUMENTS 5,704,949 A    1/1998  Prota et al.
2015/0038466 A1   2/2015  Ducki et al.

FOREIGN PATENT DOCUMENTS

JP    5-501873 A    4/1993

OTHER PUBLICATIONS

International Preliminary Report on Patentability and English translation of the Written Opinion of the International Searching Authority for International Application No. PCT/JP2018/040457, dated May 14, 2020.
Charkoudian et al., "Fe(III)-Coordination Properties of Neuromelanin Components: 5,6-Dihydroxyindole and 5,6-Dihydroxyindole-2-carboxylic Acid", Inorganic Chemistry, 2006, vol. 45, No. 9, pp. 3657-3664.
Edge et al., "Dopaquinone redox exchange with dihydroxyindole and dihydroxyindole carboxylic acid", Pigment Cell Res., 2006, 19, pp. 443-450.
International Search Report for PCT/JP2018/040457 (PCT/ISA/210) dated Jan. 29, 2019.
Tran et al., "Chemical and Structural Disorder in Eumelanins: A Possible Explanation for Broadband Absorbance", Biophysical Journal, Feb. 2006, vol. 90, (3), pp. 743-752.
Wakamatsu et al., Preparation of Eumelanin-Related Metabolites 5,6-Dihydroxyindole, 5,6-Dihydroxyindole-2-carboxylic Acid, and Their O-Methyl Derivatives, Analytical Biochemistry, 1988, 170, pp. 335-340.

*Primary Examiner* — Shawquia Jackson
(74) *Attorney, Agent, or Firm* — Birch, Stewart, Kolasch & Birch, LLP.

(57) ABSTRACT

A method for producing dihydroxyindoles includes: a step 1 of obtaining an aqueous first solution including DHIs obtained by causing DOPAs to react with hexacyanoferrate (III); a step 2 of obtaining an oleaginous second solution in which DHIs are extracted in an extraction solvent by mixing the first solution obtained in the step 1 with the extraction solvent; and a step 3 of obtaining an aqueous third solution by evaporating the extraction solvent from a mixture of the second solution obtained in the step 2 and water. The extraction of DHIs in the step 2 is performed in a tank A. After the second solution is discharged from the tank A, the second solution is supplied to a tank B, and then the step 3 is performed in the tank B.

15 Claims, 6 Drawing Sheets

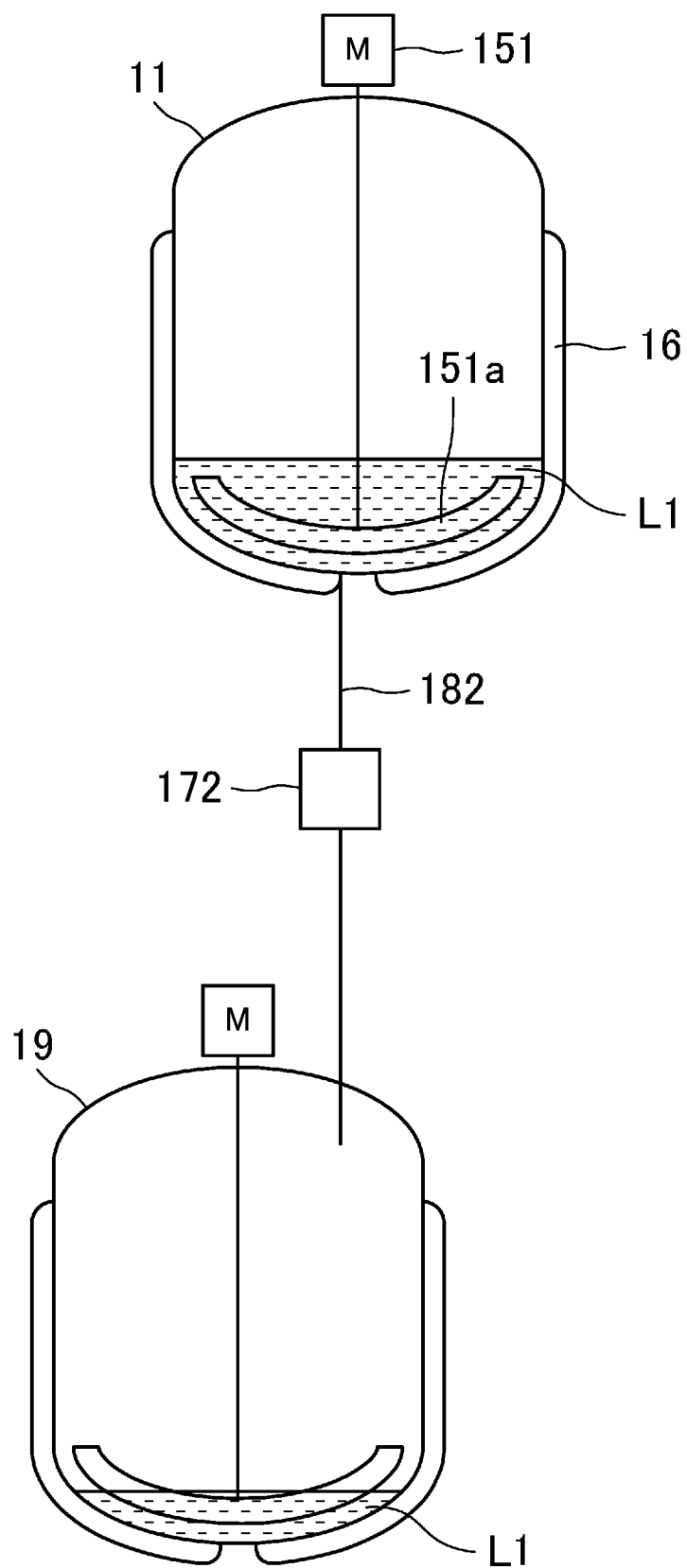

US 10,947,194 B2

METHOD FOR PRODUCING DIHYDROXYINDOLES

TECHNICAL FIELD

The present invention relates to a method for producing dihydroxyindoles.

BACKGROUND ART

Melanin is a yellow to black pigment formed in animals and plants, and is known to have an ultraviolet absorption function, a radical trapping function, an antioxidation function, and other functions. Melanin is a safe material of a biological origin, and thus, has been widely used for cosmetics, food products, plastic products, and other products. For example, melanin is used as an ultraviolet absorber in, for example, sunscreens and sunglasses, is used as an antioxidant in, for example, food and plastic products, and is used as a pigment in, for example, a hair die.

In a living body, 3-(3,4-dihydroxyphenyl)alanine (DOPA) as a substrate compound is oxidized by catalysis of tyrosinase as a melanogenesis enzyme to generate a dihydroxyindoles (e.g., 5,6-dihydroxyindole and 5,6-dihydroxyindole-2-carboxylic acid) as a melanin precursor through dopaquinone. These dihydroxyindoles are polymerized to biosynthesize melanin. The thus biosynthesized melanin is a stable macromolecular compound that is present in the form of small particles in melanin-producing cells, such as skin and hair, is insoluble in water and an organic solvent, and is not dissolved without using hot concentrated sulfuric acid or strong alkali. Thus, in the case of using melanin as a dye for fibers, leather, and the like, for example, even when melanin is used as an additive without any treatment, melanin, which is insoluble in water and an organic solvent, cannot be used for dyeing by immersion in tissues of a dyeing object. In view of this, water-soluble dihydroxyindoles are used as an additive to form melanin in a dyeing object.

As a method for producing dihydroxyindoles for use in such an application, Patent Document 1, for example, discloses a method with which hexacyanoferrate(III) is added to an aqueous solution containing 3-(3,4-dihydroxyphenyl)alanine for reaction so that dihydroxyindoles are produced, and a complex of hexacyanoferrate (II) is removed from an aqueous solution containing the obtained dihydroxyindoles. Non-patent Documents 1 and 2 disclose methods with which hexacyanoferrate(III) is added to an aqueous solution containing 3-(3,4-dihydroxyphenyl)alanine for reaction so that dihydroxyindoles are produced, and an aqueous solution containing the obtained dihydroxyindoles is supplemented with an extraction solvent of ethyl acetate to thereby extract dihydroxyindoles.

CITATION LIST

Patent Document

PATENT DOCUMENT 1: U.S. Pat. No. 5,704,949

Non-Patent Document

NON-PATENT DOCUMENT 1: Wakamatsu, K. and Ito, S. (1988) Analytical Biochemistry 170, 335-340
NON-PATENT DOCUMENT 2: R. Edge, M. d'Ischia, E. J. Land, A. Napolitano, S. Navaratham, L. Panzella, A. Pezzella, C. A. Ramsden and P. A. Riley (2006) Pigment Cell Res. 19; 443-450

SUMMARY OF THE INVENTION

The present invention relates to a method including: a step 1 of obtaining an aqueous first solution including dihydroxyindoles obtained by causing at least a material selected from the group consisting of 3-(3,4-dihydroxyphenyl)alanine and a derivative of 3-(3,4-dihydroxyphenyl)alanine to react with hexacyanoferrate(III); a step 2 of obtaining an oleaginous second solution in which the dihydroxyindoles are extracted in an extraction solvent by mixing the first solution obtained in the step 1 with the extraction solvent; and a step 3 of obtaining an aqueous third solution by evaporating the extraction solvent from a mixture of the second solution obtained in the step 2 and water, wherein the dihydroxyindoles are extracted in a tank A in the step 2, the second solution is discharged from the tank A, the second solution is supplied to a tank B, and then the step 3 is performed in the tank B.

DESCRIPTION OF EMBODIMENTS

An embodiment will be described in detail below.

A method for producing dihydroxyindoles according to an embodiment includes a reaction process (step 1), a refining process (step 2), and a solvent replacement process (step 3). In this specification, 3-(3,4-dihydroxyphenyl)alanine will be abbreviated as DOPA, one or more materials selected from the group consisting of 3-(3,4-dihydroxyphenyl)alanine and a derivative thereof will be abbreviated as DOPAs, 5,6-dihydroxyindole will be abbreviated as DHI, and dihydroxyindoles will be abbreviated as DHIs.

<Reaction Process (Step 1)>

In a reaction process, DOPAs and hexacyanoferrate(III) are caused to react with each other so that DHIs are produced, thereby obtaining an an aqueous first solution L1 including DHIs. At this time, it is suitable to mix a DOPAs solution D of a DOPAs aqueous solution or an aqueous suspension with an oxidizing agent solution O of a hexacyanoferrate(III) aqueous solution or an aqueous suspension. The reaction between DOPAs and hexacyanoferrate (III) is an oxidation-reduction reaction.

Figure 1:
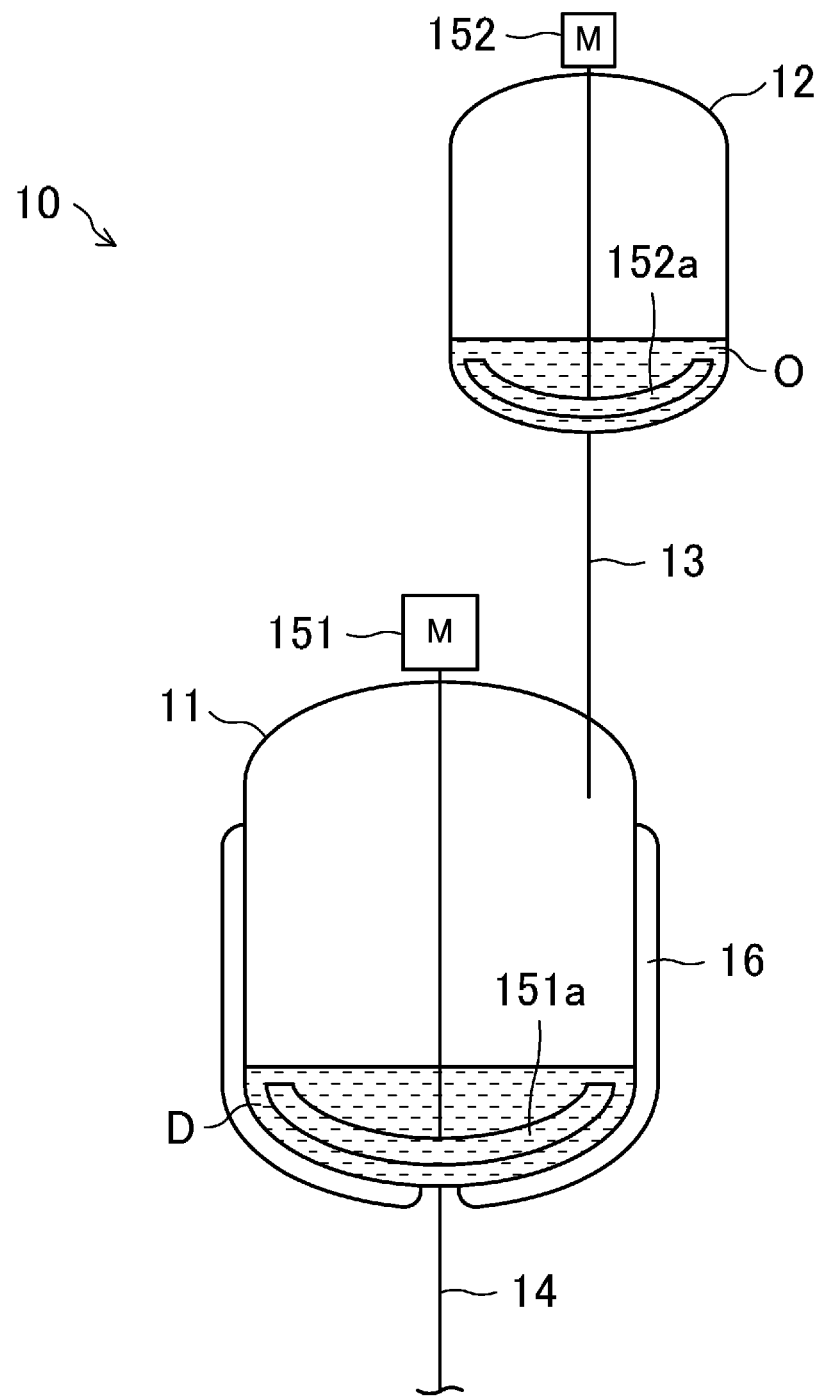
FIG. 1 A view illustrating a configuration of a reaction apparatus
FIG. 2A A view illustrating an apparatus configuration for performing circulating filtration
FIG. 2B A view illustrating an apparatus configuration for performing one-pass filtration
FIG. 3A A first illustration of a refining process
FIG. 3B A second illustration of the refining process
FIG. 4A A first illustration of a solvent replacement process
FIG. 4B A second illustration of the solvent replacement process
FIG. 4C A third illustration of the solvent replacement process
FIG. 4D A fourth illustration of the solvent replacement process

FIG. 1 illustrates an example of a reaction apparatus 10 used in the reaction process (step 1).

The reaction apparatus 10 includes a reaction tank 11 and an oxidizing agent tank 12. An oxidizing agent supply pipe 13 extending from the bottom of the oxidizing agent tank 12 is introduced into an upper portion of the reaction tank 11. A discharge pipe 14 extends from the bottom of the reaction tank 11. The reaction tank 11 and the oxidizing agent tank 12 are provided with agitators 151 and 152, respectively. Agitating impellers 151a and 152a of the agitators 151 and 152 only need to sufficiently agitate a low-viscosity solution, and may be, for example, paddle impellers, disc turbines, tilt paddle impellers, or anchor impellers. The reaction tank 11 is provided with a jacket 16 for adjusting the temperature in the tank.

Specifically, first, water is poured into the reaction tank 11. Water is suitably ion-exchanged water or distilled water, for example. It is suitable to use water whose dissolved oxygen concentration has been reduced by supplying an inert gas such as a nitrogen gas or an argon gas. The dissolved oxygen concentration of water is suitably 1.0 mg/L or less, and more suitably 0.5 mg/L or less. The dissolved oxygen concentration of this water is measured with a commercially available dissolved oxygen meter (the same hereinafter).

In the reaction tank 11, before or after pouring water, the oxygen concentration is suitably reduced by supplying an inert gas such as a nitrogen gas or an argon gas. The oxygen concentration of a gaseous phase in the reaction tank 11 is suitably 1.0% by volume or less, and more suitably 0% by volume. The oxygen concentration of the gaseous phase in the reaction tank 11 is measured with a commercially available oxygen concentration meter (the same hereinafter). The supply of the inert gas to the gaseous phase in the reaction tank 11 is suitably continuously performed during an operation in this reaction process.

Next, while water is agitated by starting the agitator 151 disposed in the reaction tank 11, DOPAs are supplied to be dissolved or dispersed, thereby obtaining a DOPAs solution D. This method for preparing the DOPAs solution D is a suitable specific example, and may be a method in which DOPAs are first supplied in the reaction tank 11 and then water is supplied to the reaction tank 11, a method in which water and DOPAs are supplied to the reaction tank 11 at the same time, or a method in which each of water and DOPAs is divided into parts and these parts are alternately supplied to the reaction tank 11.

Examples of a DOPA among DOPAs include D-DOPA (3,4-dihydroxy-D-phenylalanine) and L-DOPA (3,4-dihydroxy-L-phenylalanine). Examples of a DOPA derivative among DOPAs include 2-3',4'-dihydroxyphenyl ethylamine derivatives (e.g., N-octanoyl-4-(2-aminoethyl)benzene-1,2-diol and N-octanoyl-4,2-(3,4-dihydropheny)ethylamine), 4-(2-aminoethyl)benzene-1,2-diol(dopamine), salt of D-DOPA (e.g., potassium salt and sodium salt), salt of L-DOPA (e.g., potassium salt and sodium salt), lower (carbon number of 1 to 4) alkyl ester of DOPA, α-lower (carbon number of 1 or more and 4 or less) alkyl DOPA, and isomers thereof. The DOPAs solution D may contain a chemical substance that is inactive to DOPAs such as benzoates, as well as DOPAs.

The content of DOPAs in the DOPAs solution D is suitably 0.10% by mass or more, more suitably 0.20% by mass or more, and much more suitably 0.30% by mass or more, from the viewpoint of obtaining high productivity, and is suitably 1.0% by mass or less, more suitably 0.70% by mass or less, and much more suitably 0.50% by mass or less, from the viewpoint of enhancing the yield of DHIs while suppressing progress of a side reaction. The content of DOPAs in the DOPAs solution D is suitably 0.10% by mass or more and 1.0% by mass or less, more suitably 0.20% by mass or more and 0.70% by mass or less, and much more suitably 0.30% by mass or more and 0.50% by mass or less.

In addition, water is poured into the oxidizing agent tank 12. Water is suitably ion-exchanged water or distilled water, for example. It is suitable to use water whose dissolved oxygen concentration has been reduced by supplying an inert gas such as a nitrogen gas or an argon gas. The dissolved oxygen concentration of water is suitably 1.0 mg/L or less, and more suitably 0.5 mg/L or less.

Thereafter, while water is agitated by starting the agitator 152 disposed in the oxidizing agent tank 12, hexacyanoferrate(III) is placed and dissolved or dispersed, thereby obtaining an oxidizing agent solution O.

Examples of hexacyanoferrate(III) include alkali metal salt of hexacyanoferrate(III) acid, such as potassium hexacyanoferrate(III) acid, sodium hexacyanoferrate(III) acid, and lithium hexacyanoferrate(III) acid. As hexacyanoferrate(III), one or more of these materials are suitably used.

The content of hexacyanoferrate(III) in the oxidizing agent solution O with respect to the mole number of DOPAs in the DOPAs solution D is suitably 2.0 equivalents or more, more suitably 2.6 equivalents or more, and much more suitably 3.5 equivalents or more, from the viewpoint of enhancing the yield of DHIs while promoting a reaction, and is suitably 6.0 equivalents or less, more suitably 5.5 equivalents or less, and much more suitably 4.6 equivalents or less, from the viewpoint of enhancing the yield of DHIs while suppressing progress of a side reaction. The content of hexacyanoferrate(III) in the oxidizing agent solution O with respect to the mole number of DOPAs in the DOPAs solution D is suitably 2.0 equivalents or more and 6.0 equivalents or less, more suitably 2.6 equivalents or more and 5.5 equivalents or less, and much more suitably 3.5 equivalents or more and 4.6 equivalents or less.

The oxidizing agent solution O suitably includes a base agent, from the viewpoint of promoting a reaction while maintaining the pH during the reaction at a weak basicity. Examples of the base agent include alkali metal salt of hydrogencarbonate ions, such as potassium hydrogencarbonate and sodium hydrogencarbonate, and alkali metal salt of carbonate ions, such as potassium carbonate and sodium carbonate. As the base agent, one or more of these materials are suitably used. The oxidizing agent solution O may additionally include a chemical substance that is inactive to hexacyanoferrate(III) such as benzoates.

From the viewpoint of promoting a reaction by maintaining the pH during the reaction at a moderate weak basicity, the content of the base agent in the oxidizing agent solution O with respect to the mole number of DOPAs in the DOPAs solution D is suitably 3.9 equivalents or more, more suitably 5.1 equivalents or more, and much more suitably 5.9 equivalents or more, and from a similar viewpoint, is suitably 9.0 equivalents or less, more suitably 7.8 equivalents or less, and much more suitably 6.3 equivalents or less The content of the base agent in the oxidizing agent solution O with respect to the mole number of DOPAs in the DOPAs solution D is suitably 3.9 equivalents or more and 9.0 equivalents or less, more suitably 5.1 equivalents or more and 7.8 equivalents or less, and much more suitably 5.9 equivalents or more and 6.3 equivalents or less.

Subsequently, while the DOPAs solution D is agitated with the agitator 151 in the reaction tank 11, the oxidizing agent solution O is dropped into the DOPAs solution D in the reaction tank 11 from the oxidizing agent tank 12 through the oxidizing agent supply pipe 13.

From the viewpoint of application possibility to mass production, the time of dropping of the oxidizing agent solution O is suitably one minute or more, more suitably 3 minutes or more, and much more suitably 5 minutes or more, and from the viewpoint of enhancing the yield of DHIs while suppressing progress of a side reaction, is suitably one hour or less, more suitably 30 minutes or less, and much more suitably 10 minutes or less. The time of dropping of the oxidizing agent solution O is suitably one minute or more and one hour or less, more suitably 3 minutes or more and 30 minutes or less, and much more suitably 5 minutes or more and 10 minutes or less.

Then, by the dropping of the oxidizing agent solution O into the DOPAs solution D, the oxidation-reduction reaction between DOPAs and hexacyanoferrate(III) is caused to progress to thereby produce DHIs. Although the oxidizing agent solution O from the oxidizing agent tank 12 is added to the DOPAs solution D in the reaction tank 11 in this embodiment, the technique disclosed here is not limited to this example as long as the DOPAs solution D and the oxidizing agent solution O are mixed. For example, the DOPAs solution D may be added to the oxidizing agent solution O, or the DOPAs solution D and the oxidizing agent solution O may be supplied to a solution tank at the same time or alternately.

From the viewpoint of reducing the reaction time by increasing the reaction rate, the reaction temperature of DOPAs and hexacyanoferrate(III) is suitably 10° C. or more, more suitably 25° C. or more, and much more suitably 30° C. or more, and from the viewpoint of enhancing the yield of DHIs while suppressing progress of a side reaction, is suitably 50° C. or less, more suitably 45° C. or less, and much more suitably 40° C. or less. The reaction temperature of DOPAs and hexacyanoferrate(III) is suitably 10° C. or more and 50° C. or less, and more suitably 25° C. or more and 45° C. or less, and much more suitably 30° C. or more and 40° C. or less. This reaction temperature can be controlled by setting a liquid temperature with the jacket 16 disposed on the reaction tank 11, and in preparation of the DOPAs solution D in the reaction tank 11, the liquid temperature of the DOPAs solution D is suitably set at this reaction temperature.

From the viewpoint of enhancing the yield of DHIs, the reaction time (aging time) of DOPAs and hexacyanoferrate (III) is suitably 2 hours or more, more suitably 3 hours or more, and much more suitably 4 hours or more, from the start of dropping of the oxidizing agent solution 0, and from the viewpoint of enhancing productivity, is suitably 22 hours or less, more suitably 6 hours or less, and much more suitably 5 hours or less. The reaction time of DOPAs and hexacyanoferrate(III) is suitably 2 hours or more and 22 hours or less, more suitably 3 hours or more and 6 hours or less, and much more suitably 4 hours or more and 5 hours or less.

The produced DHIs depend on DOPAs as raw materials, and examples of the DHIs include DHI, salt thereof (e.g., potassium salt and sodium salt), 5,6-dihydroxyindole-2-carboxylic acid, and salt thereof (e.g., potassium salt and sodium salt). DHIs suitably include one or more of these materials.

In the manner described above, in the reaction tank 11, the aqueous first solution L1 containing DHIs is obtained.

From the viewpoint of stabilizing DHIs, the obtained first solution L1 is suitably subjected to pH adjustment by adding a pH adjuster. Examples of the pH adjuster include a phosphoric acid aqueous solution, dilute sulfuric acid, and diluted hydrochloric acid. As the pH adjuster, one or more of these materials are suitably used. From the viewpoint of enhancing the yield by stabilizing DHIs, the pH of the first solution L1 after the pH adjustment is suitably 3.0 or more, more suitably 3.3 or more, and much more suitably 3.5 or more, and from the viewpoint of enhancing a filtration rate during filtration described later and obtaining an excellent phase split at extraction, is suitably 5.5 or less, more suitably 5.3 or less, and much more suitably 5.0 or less. The pH of the first solution L1 after the pH adjustment is suitably 3.0 or more and 5.5 or less, more suitably 3.3 or more and 5.3 or less, and much more suitably 3.5 or more and 5.0 or less.

Figure 2A:
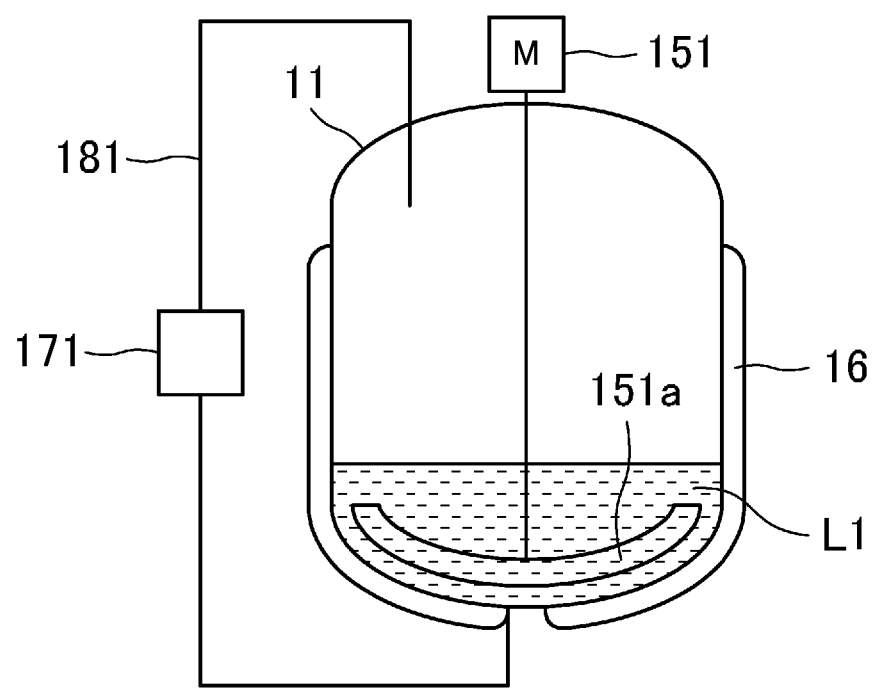

The obtained first solution L1 is suitably subjected to filtration from the viewpoint of removing impurities. As illustrated in FIG. 2A, a filtration method can be a method in which a circulation pipe 181 provided with a filter 171 is disposed in the reaction tank 11, where the first solution L1 is caused to circulate for circulating filtration, and the resulting first solution L1, which is a filtrate after the filtration, is stored in the reaction tank 11. As illustrated in FIG. 2B, in another method, a filtration pipe 182 extending from the reaction tank 11 is provided with a filter 172, and the filtration pipe 182 is connected to a filtrate tank 19. The first solution L1 is distributed for one-pass filtration in the filtrate tank 19, and the resulting first solution L1, which is a filtrate after the filtration, is stored in the filtrate tank 19. From the viewpoint of increasing the filtration rate, the aperture of a filter medium disposed in each of the filters 171 and 172 is suitably 0.1 µm or more, more suitably 0.5 µm or more, and much more suitably 1.0 µm or more, and from the viewpoint of removing impurities, is suitably 5.0 µm or less, more suitably 2.0 µm or less, and much more suitably 1.5 µm or less. The aperture of the filter medium disposed in each of the filters 171 and 172 is 0.1 µm or more and 5.0 µm or less, more suitably 0.5 µm or more and 2.0 µm or less, and much more suitably 1.0 µm or more and 1.5 µm or less. The filter medium is not limited to a specific material from the viewpoint of removing a water-insoluble by-product, but is suitably made of a hydrophilic material from the viewpoint of increasing the filtration rate.

<Refining Process (Step 2)>

In the refining process (step 2), the first solution L1 obtained in the reaction process (step 1) is mixed with an extraction solvent so that DHIs are extracted in the extraction solvent, thereby obtaining an oleaginous second solution L2.

Figure 3A:
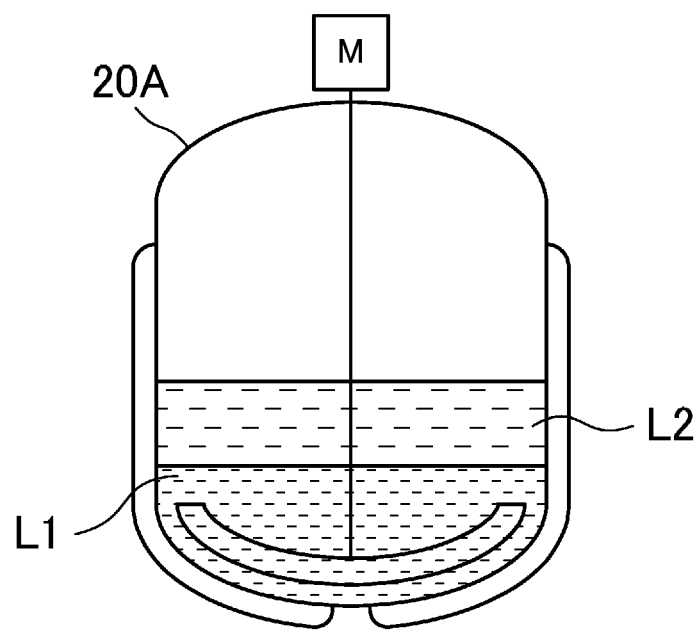
Figure 3B:
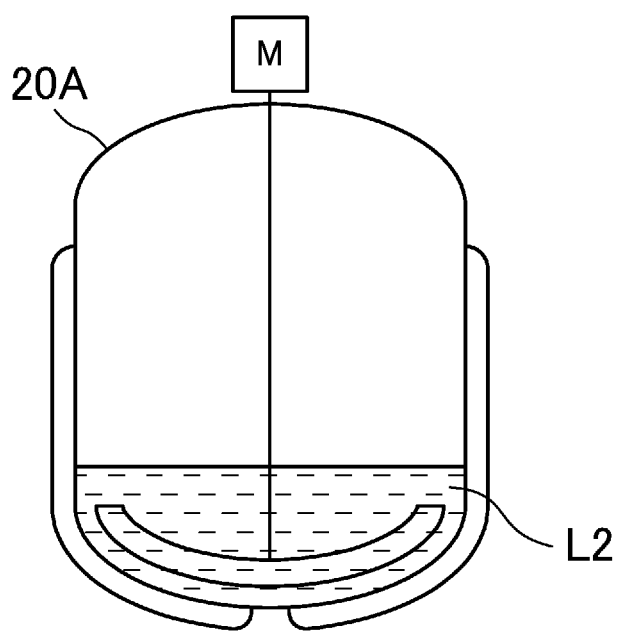

As a specific example, as illustrated in FIG. 3A, in a tank A 20A in which the first solution L1 obtained in the reaction process is stored, an extraction solvent is added while the first solution L1 is agitated so that DHIs are extracted in the extraction solvent, and at this time, the solution is separated in phase into: a lower layer of a water-phase first solution L1 in which cyanide remains; and an upper layer of an oil-phase second solution L2 in which DHIs are extracted in the extraction solvent, and then, as illustrated in FIG. 3B, the lower layer of the first solution L1 is discharged from the bottom of the tank A 20A, thereby obtaining the oleaginous second solution L2. Here, the tank A 20A may be the reaction tank 11 used in the reaction process and illustrated in FIGS. 1 and 2A, may be the filtrate tank 19 illustrated in FIG. 2B, or may be another solution tank to which the first solution L1 is then transferred. Although the extraction solvent is added to the first solution L1 in the configuration of this embodiment, in the case of transferring the first solution L1 from the reaction tank 11, the technique disclosed here is not limited to this configuration as long as the first solution L1 is mixed with the extraction solvent. For example, the first solution L1 may be added to the extraction solvent, or the first solution L1 and the extraction solvent may be added to the solution tank at the same time or alternately.

In the tank A 20A, the oxygen concentration is suitably reduced by supplying an inert gas such as a nitrogen gas or an argon gas. The oxygen concentration of the gaseous phase in the tank A 20A is suitably 1.0% by volume or less, and more suitably 0% by volume. The supply of the inert gas to the gaseous phase in the tank A 20A is suitably continuously performed during an operation of this refining process.

From the viewpoint of layer separation, the extraction solvent is suitably an organic solvent having an octanol/water distribution coefficient (Log P) of 0 (zero) or more and 4.0 or less. Examples of the extraction solvent include: ethyl acetate (0.73) and diethyl ether (0.89) that are organic solvents each having an octanol/water distribution coefficient less than 0.90; methyl isobutyl ketone (1.4), dichloromethane (1.3), and cyclohexane (3.4) that are organic solvents each having an octanol/water distribution coefficient larger than 0.90 (values in parentheses are octanol/water distribution coefficients). As the extraction solvent, one or more of these materials are suitably used, and from the viewpoint of enhancing extraction efficiency, it is suitable for the extraction solvent to include an organic solvent having an octanol/water distribution coefficient of 1.5 or less, and more suitably less than 0.90, and it is much more suitable for the extraction solvent to include ethyl acetate. A chemical substance that is inactive to DHIs such as benzoates and phosphates may be added to the first solution L1, as well as the extraction solvent.

From the viewpoint of enhancing the yield of DHIs, the mixture amount of the extraction solvent in the first solution L1 with respect to the volume of the first solution L1 at the end of the reaction is suitably 20% by volume or more, more suitably 30% by volume or more, and much more suitably 50% by volume, and from the viewpoint of reducing manufacturing costs by reducing the waste liquid amount, is suitably 400% by volume or less, more suitably 200% by volume or less, and much more suitably 100% by volume or less. The mixture amount of the extraction solvent in the first solution L1 is suitably 20% by volume or more and 400% by volume or less, more suitably 30% by volume or more and 200% by volume or less, and much more suitably 50% by volume or more and 100% by volume or less, with respect to the volume of the first solution L1 at the end of the reaction.

From the viewpoint of enhancing the yield of DHIs, it is suitable to agitate a mixed solution of the first solution L1 and the extraction solvent after or at the same time as addition of the extraction solvent to the first solution L1.

In the case of agitating the mixed solution after the addition of the extraction solvent, from the viewpoint of enhancing the yield of DHIs, the agitation time (extraction time) of the mixed solution is suitably 10 minutes or more, more suitably 15 minutes or more, and much more suitably 20 minutes or more, and from the viewpoint of enhancing productivity, is suitably 120 minutes or less, more suitably 90 minutes or less, and much more suitably 60 minutes or less. The agitation time (extraction time) of the mixed solution is suitably 10 minutes or more and 120 minutes or less, more suitably 15 minutes or more and 90 minutes or less, and much more suitably 20 minutes or more and 60 minutes or less.

In the case of agitating the first solution L1 while adding the extraction solvent, from the viewpoint of enhancing the yield of DHIs, the agitation time (extraction time) of the first solution L1 from the start of addition of the extraction solvent is suitably 10 minutes or more, more suitably 15 minutes or more, and much more suitably 20 minutes or more, and from the viewpoint of enhancing productivity, is suitably 120 minutes or less, more suitably 90 minutes or less, and much more suitably 60 minutes or less. The agitation time (extraction time) of the first solution L1 is suitably 10 minutes or more and 120 minutes or less, more suitably 15 minutes or more and 90 minutes or less, and much more suitably 20 minutes or more and 60 minutes or less.

After mixing of the extraction solvent, from the viewpoint of removing impurities, the oleaginous second solution L2 is suitably set apart from an aqueous solution, and from the viewpoint of further removing impurities, the obtained second solution L2 is then suitably cleaned with wash water. The cleaning method may be a method in which in the tank A 20A storing the obtained second solution L2, wash water is brought into sufficient contact with the second solution L2 by adding wash water while agitating the second solution L2, and then, the lower-layer water phase out of the upper-layer oil phase of the second solution L2 and the lower-layer water phase subjected to phase separation is discharged from the bottom of the tank A 20A.

From the viewpoint of maintaining the pH of wash water around neutral with stability, the amount of addition of wash water to the second solution L2 is suitably 10% by volume or more, more suitably 20% by volume or more, and much more suitably 30% by volume or more, and from the viewpoint of enhancing the yield of DHIs, is suitably 100% by volume or less, more suitably 80% by volume or less, and much more suitably 50% by volume or less. The amount of addition of wash water to the second solution L2 with respect to the volume of the second solution L2 is suitably 10% by volume or more and 100% by volume or less, more suitably 20% by volume or more and 80% by volume or less, and much more suitably 30% by volume or more and 50% by volume or less.

From the viewpoint of maintaining the pH of wash water around neutral with stability, the cleaning time of the second solution L2 with wash water is suitably 30 minutes or more, more suitably 45 minutes or more, and much more suitably 60 minutes or more, and from the viewpoint of enhancing the yield of DHIs, is suitably 120 minutes or less, more suitably 105 minutes or less, and much more suitably 90 minutes or less. The cleaning time of the second solution L2 with wash water is suitably 30 minutes or more and 120 minutes or less, more suitably 45 minutes or more and 105 minutes or less, and much more suitably 60 minutes or more and 90 minutes or less.

From the viewpoint of maintaining the pH around neutral, wash water may contain polybasic acid salt. Examples of the polybasic acid salt include potassium salt of phosphoric acid, potassium salt of citric acid, potassium salt of carbonic acid, sodium salt of phosphoric acid, sodium salt of citric acid, and sodium salt of carbonic acid. As the polybasic acid, one or more of these materials is suitably used, and more suitably, the polybasic acid includes potassium salt of phosphoric acid (dipotassium hydrogen phosphate and dipotassium hydrogen phosphate).

<Solvent Replacement Process (Step 3)>

In the solvent replacement process (step 3), the second solution L2 obtained in the refining process (step 2) is mixed with water W and an extraction solvent is evaporated to thereby perform solvent displacement, thereby obtaining a DHIs solution of an aqueous solution or an aqueous dispersion containing DHIs as an aqueous third solution L3. From the viewpoint of efficiency in production, concentration adjustment is suitably performed together with the solvent displacement.

Specifically, first, the second solution L2 obtained in the refining process is discharged from the tank A 20A and transferred, and then, the second solution L2 is supplied to and stored in the tank B 20B.

Figure 4A:
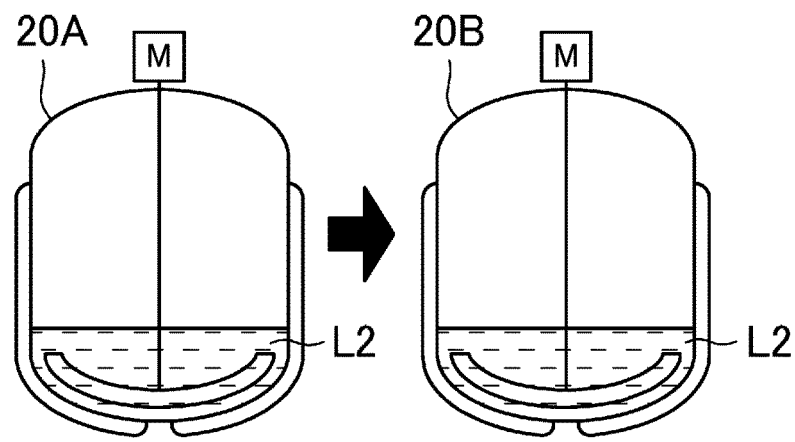

At this time, as illustrated in FIG. 4A, the second solution L2 obtained in the refining process may be discharged from the tank A 20A and supplied to and stored in another tank B 20B different from the tank A 20A. Here, the tank B 20B is suitably a solution tank in which substantially no cyanide is attached to the inner wall of the tank through cleaning of the inside of the tank, and is more suitably a solution tank in which the inside of the tank is cleaned with water.

Figure 4B:
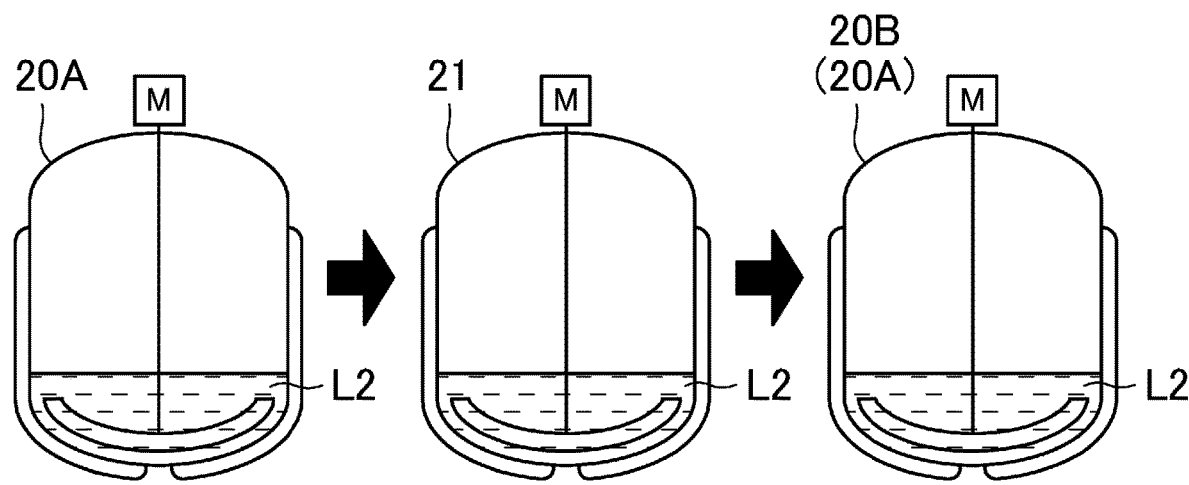

As also illustrated in FIG. 4B, in an alternative example, the second solution L2 obtained in the refining process is discharged from the tank A 20A and temporarily supplied to and stored in another clean solution tank 21, whereas after the refining process and discharge of the second solution L2, the inside of the tank A 20A is cleaned to substantially eliminate a remaining residue of cyanide on the inner wall, and the resulting tank A 20A subjected to the cleaning is used as a tank B 20B so that the second solution L2 is supplied from the solution tank 21 to the tank B 20B (tank A 20A) and stored therein. The inside of the tank A 20A used as the tank B 20B is suitably cleaned with water.

The method for cleaning the inside of the tank is not limited to a specific method. As a cleaning method, a cleaning solution may be stored and agitated in the tank, a cleaning solution may be sprayed to the inner wall of the tank, or the inner wall of the tank may be rubbed with a cleaning tool such as a brush.

In the tank B 20B, the oxygen concentration is suitably reduced by supplying an inert gas such as a nitrogen gas or an argon gas. The oxygen concentration of the gaseous phase in the tank B 20B is suitably 1.0% by volume or less and more suitably 0% by volume. The supply of the inert gas to the gaseous phase in the tank B 20B is suitably continuously performed during an operation of this solvent replacement process.

Next, water W is added to the second solution L2. Although water W is added after the second solution L2 is supplied to the tank B 20B in the configuration of this embodiment, the technique disclosed here is not limited to this configuration as long as the second solution L2 is mixed with water W. For example, the second solution L2 may be added after water W is supplied to the tank B 20B, or the second solution L2 and water W may be supplied to the solution tank B 20B at the same time or alternately.

Figure 4C:
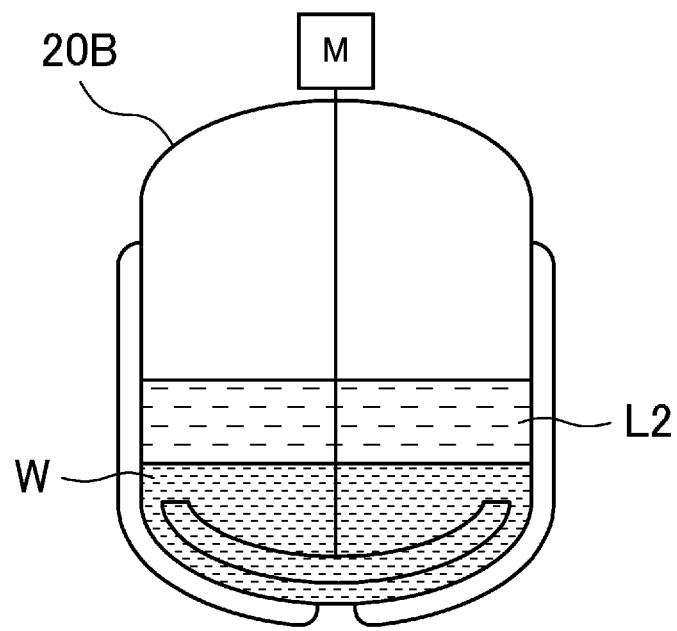

Subsequently, as illustrated in FIG. 4C, the second solution L2 to which water W is added is heated in the tank B 20B so that an extraction solvent is evaporated and the extraction solvent is displaced by water W by solvent displacement. From the viewpoint of reducing the concentration of an organic solvent, this solvent displacement by addition of water W and evaporation of the extraction solvent is suitably performed a plurality of times. The number of solvent displacements is suitably two or more and four or less.

Water W to be added is, for example, ion-exchanged water or distilled water. Water W is suitably water whose dissolved oxygen concentration has been reduced by supplying an inert gas such as a nitrogen gas or an argon gas. The dissolved oxygen concentration of water W is suitably 1.0 mg/L or less and more suitably 0.5 mg/L or less.

First addition of water W to the second solution L2 at the first solvent displacement may be performed on the second solution L2 supplied to the tank B 20B, or may be performed on the second solution L2 that has been discharged from the tank A 20A and has not yet been supplied to the tank B 20B. Addition of water W at the second and subsequent solvent displacements is performed on liquid remaining in the tank B 20B.

From the viewpoint of efficiently performing solvent displacement, the amount of addition of water W with respect to the volume of the second solution L2 in the first solvent displacement or with respect to the volume of the liquid remaining in the tank B 20B in the second and subsequent solvent displacements, is suitably 50% by volume or more, more suitably 80% by volume or more, and much more suitably 100% by volume or more, and from a similar viewpoint, is suitably 150% by volume or less, more suitably 120% by volume or less, and much more suitably 110% by volume or less. The amount of addition of water W with respect to the volume of the second solution L2 in the first solvent displacement or the volume of liquid remaining in the tank B 20B in the second and subsequent solvent displacements, is suitably 50% by volume or more and 150% by volume or less, more suitably 80% by volume or more and 120% by volume or less, and much more suitably 100% by volume or more and 110% by volume or less.

From the viewpoint of increasing an evaporation rate of the extraction solvent, the liquid temperature in evaporating the extraction solvent is suitably 40° C. or more, more suitably 50° C. or more, and much more suitably 60° C. or more, and from the viewpoint of suppressing thermal decomposition of DHIs, is suitably 90° C. or less, more suitably 85° C. or less, and much more suitably 80° C. or less. The liquid temperature in evaporating the extraction solvent is suitably 40° C. or more and 90° C. or less, more suitably 50° C. or more and 85° C. or less, and much more suitably 60° C. or more and 80° C. or less. Steam of the evaporated extraction solvent is suitably condensed by, for example, a heat exchanger, and collected.

From the viewpoint of increasing an evaporation rate of the extraction solvent, the pressure in evaporating the extraction solvent in the first solvent displacement is suitably an atmospheric pressure (101.325 kPa (abs)) or less, more suitably 90 kPa (abs) or less, and much more suitably 80 kPa (abs) or less. From the viewpoint of increasing an evaporation rate of the extraction solvent, the pressure in evaporating the extraction solvent in the second and subsequent solvent displacements is suitably 80 kPa (abs) or less, more suitably 40 kPa (abs) or less, and much more suitably 10 kPa (abs) or less.

Figure 4D:
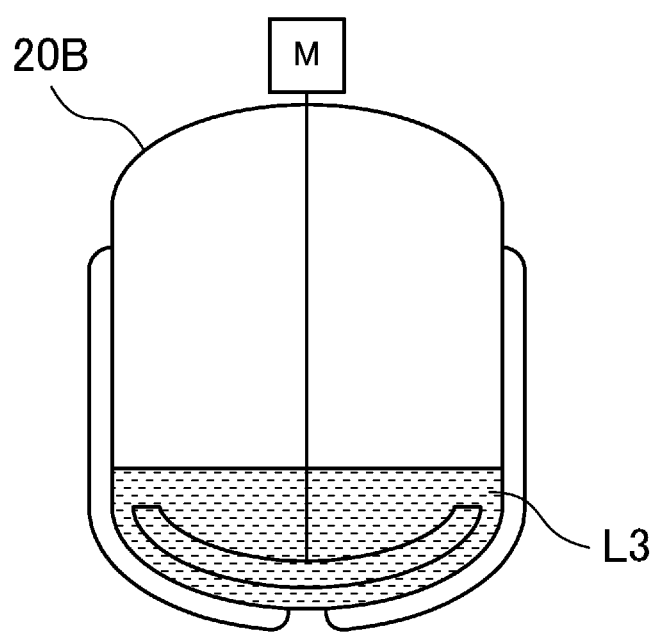

Then, as illustrated in FIG. 4D, water and a water-soluble solvent are added to liquid remaining in the tank B 20B after solvent displacement and the concentration is adjusted so that DHIs can be obtained in the form of a DHIs solution, which is the aqueous third solution L3. Examples of the water-soluble solvent include ethanols.

The content of DHIs in the DHIs solution of the obtained third solution L3 is suitably 0.3% by mass or more, more suitably 0.5% by mass or more, and much more suitably 1.0% by mass or more. The content of DHIs is measured by high performance liquid chromatography (HPLC).

The total cyan concentration in the DHIs solution of the obtained third solution L3 is suitably 10 mg/L or less, more suitably 5 mg/L or less, much more suitably 1 mg/L or less, and much more suitably 0.5 mg/L or less. The total cyan concentration is the content of all the cyans in cyanide ions, hydrogen cyanide, metallocyanide, metal cyano complex, and organic cyano compounds in the third solution L3, and is measured by a picric acid method.

In the DHIs solution of the obtained third solution L3, the cyan content with respect to 1 (one) mass part of DHIs is suitably 10 mg/L or less, more suitably 5 mg/L or less, and much more suitably 1 mg/L or less. The cyan amount is measured by a picric acid method.

The content of the organic solvent in the DHIs solution of the obtained third solution L3 is suitably 1.5% by mass or less, more suitably 1.0% by mass or less, and much more suitably 0.5% by mass or less. The content of the organic solvent is measured by gas chromatography (GC).

In a case where the DHIs solution of the third solution L3 after solvent displacement is used for dyeing such as hair dyeing, the content of DHIs is suitably about 1% by mass. Thus, from this viewpoint, the second solution L2 is suitably condensed before solvent displacement.

The condensation of the second solution L2 may be performed in such a manner that the second solution L2 obtained in the refining process is condensed by evaporating the extraction solvent in the tank A 20A and then the condensed second solution L2 is discharged from the tank A 20A and supplied to and stored in the tank B 20B. Alternatively, the condensation may be performed in such a manner that the second solution L2 obtained in the refining process is discharged from the tank A 20A and is supplied to and stored in the tank B 20B, and then, the second solution L2 is condensed by evaporating the extraction solvent in the tank B 20B. The condensation may also be performed in such a manner that the second solution L2 obtained in the refining process is discharged from the tank A 20A and is supplied to another solution tank and condensed by evaporating the extraction solvent, and then the resulting solution is discharged from the solution tank so that the condensed second solution L2 is supplied to and stored in the tank B 20B.

From the viewpoint of increasing an evaporation rate of the extraction solvent, the liquid temperature in condensing the second solution L2 is suitably 40° C. or more, more suitably 50° C. or more, and much more suitably 60° C. or more, and from the viewpoint of suppressing thermal decomposition of DHIs, is suitably 90° C. or less, more suitably 85° C. or less, and much more suitably 80° C. or less. The liquid temperature in condensing the second solution L2 is suitably 40° C. or more and 90° C. or less, more suitably 50° C. or more and 85° C. or less, and much more suitably 60° C. or more and 80° C. or less.

From the viewpoint of increasing an evaporation rate of the extraction solvent, the pressure in condensing the second solution L2 is suitably an atmospheric pressure (101.325 kPa (abs)) or less, more suitably 100 kPa (abs) or less, and much more suitably 90 kPa (abs) or less.

To use dihydroxyindoles produced in the methods disclosed in Non-patent Documents 1 and 2 as an additive, it is necessary to reduce the contents of cyanide and an organic solvent, from the viewpoint of ensuring safety to the human body. Among these materials, the content of cyanide can be reduced by extracting dihydroxyindoles by using an extraction solvent from an aqueous solution containing dihydroxyindoles. The content of the extraction solvent as an organic solvent can be reduced through solvent displacement by evaporating the extraction solvent and adding water. However, it was found that the solvent displacement of the extraction solvent with water has the problem of an increase in the content of cyanide that was expected to be reduced.

On the other hand, in the method for producing DHIs according to the foregoing embodiment, extraction of DHIs in the refining process is performed in the tank A 20A and the second solution L2 is discharged from the tank A 20A and then supplied to the tank B 20B, and solvent displacement in the solvent replacement process is performed in the tank B 20B so that it is possible to suppress an increase in the content of cyanide in solvent displacement of the extraction solvent with water W in the solvent displacement process after extraction of DHIs in the extraction solvent in the refining process.

Although the reason for this is not clear, in a case where the extraction of DHIs in the refining process is performed in the tank A 20A and then solvent displacement in the solvent replacement process is performed in the tank A 20A, it is supposed that the aqueous first solution L1 containing cyanide contacts the inner wall of the tank A 20A so that cyanide adheres to the inner wall in the refining process, and cyanide adhering to the inner wall of the tank A 20A is dissolved again in water added for solvent displacement in the solvent replacement process, and thus, the content of cyanide that was expected to be reduced by extraction of DHIs in the extraction solvent increases after the solvent displacement. In view of this, in the method for producing DHIs according to this embodiment, extraction of DHIs in the refining process is performed in the tank A 20A, the second solution L2 is discharged from the tank A 20A and supplied to the tank B 20B in which substantially no cyanide adheres to the inner wall thereof, and in this tank B 20B, solvent displacement in the solvent replacement process is performed. Thus, it is expected that cyanide is not dissolved in water W added for the solvent displacement, and an increase in the content of cyanide after the solvent replacement process can be suppressed.

In regard to the embodiment described above, the following configuration will be described.

<1> A method for producing DHIs including: a step 1 of obtaining an aqueous first solution including DHIs obtained by causing DOPAs and hexacyanoferrate(III) to react with each other; a step 2 of obtaining an oleaginous second solution in which the DHIs are extracted in the extraction solvent by mixing the first solution obtained in the step 1 with an extraction solvent; and a step 3 of obtaining an aqueous third solution by evaporating the extraction solvent from a mixture of the second solution obtained in the step 2 and water, the DHIs are evaporated in a tank A in the step 2, after the second solution is discharged from the tank A, the second solution is supplied to a tank B, and the step 3 is performed in the tank B.

<2> The method described in <1> in which the DOPAs include one or more of D-DOPA, L-DOPA, 2-3',4'-dihydroxyphenylethylamine derivative, 4-(2-aminoethyl)benzene-1,2-diol, potassium salt and sodium salt of D-DOPA, potassium salt and sodium salt of L-DOPA, lower (carbon number of 1 to 4) alkyl ester of DOPA, α-lower (carbon number of 1 or more and 4 or less) alkyl DOPA, and isomers thereof.

<3> The method described in <1> or <2> in which the hexacyanoferrate(III) includes one or more of potassium hexacyanoferrate(III), sodium hexacyanoferrate(III), and lithium hexacyanoferrate(III).

<4> The method described in any one of <1> to <3> in which the step 1, a DOPAs solution of an aqueous solution or an aqueous suspension including the DOPAs is mixed with an oxidizing agent solution of an aqueous solution or an aqueous suspension including the hexacyanoferrate(III).

<5> The method described in <4> in which a content of the DOPAs in the DOPAs solution is suitably 0.10% by mass or more, more suitably 0.20% by mass or more, and much more suitably 0.30% by mass or more, and is suitably 1.0% by mass or less, more suitably 0.7% by mass or less, and much more suitably 0.50% by mass or less.

<6> The method described in <4> or <5> in which a content of the hexacyanoferrate(III) in the oxidizing agent solution with respect to a mole number of the DOPAs in the DOPAs solution is suitably 2.0 equivalents or more, more suitably 2.6 equivalents or more, and much more suitably 3.5 equivalents or more, and is suitably 6.0 equivalents or less, more suitably 5.5 equivalents or less, and much more suitably 4.6 equivalents or less.

<7> The method described in any one of <4> to <6> in which the oxidizing agent solution includes a base agent.

<8> The method described in <7> in which the base agent includes one or more of potassium hydrogencarbonate, sodium hydrogencarbonate, potassium carbonate, and sodium carbonate.

<9> The method described in <7> or <8> in which a content of the base agent in the oxidizing agent solution with respect to a mole number of DOPAs in the DOPAs solution is suitably 3.9 equivalents or more, more suitably 5.1 equivalents or more, and much more suitably 5.9 equivalents or more, and is suitably 9.0 equivalents or less, more suitably 7.8 equivalents or less, and much more suitably 6.3 equivalents or less.

<10> The method described in any one of <4> to <9> in which the oxidizing agent solution is dropped in the DOPAs solution while the DOPAs solution is agitated.

<11> The method described in <10> in which a time of dropping of the oxidizing agent solution is suitably one minute or more, more suitably three minutes or more, and much more suitably five minutes or more, and is suitably one hours or less, more suitably 30 minutes or less, and much more suitably 10 minutes or less.

<12> The method described in any one of <1> to <11> in which a reaction temperature of the DOPAs and the hexacyanoferrate(III) is suitably 10° C. or more, more suitably 25° C. or more, and much more suitably 30° C. or more, and is suitably 50° C. or less, more suitably 45° C. or less, and much more suitably 40° C. or less.

<13> The method described in any one of <1> to <12> in which the DHIs include one or more of DHI, potassium salt and sodium salt of DHI, 5,6-dihydroxyindole-2-carboxylic acid, and potassium salt and sodium salt of 5,6-dihydroxyindole-2-carboxylic acid.

<14> The method described in any one of <1> to <13> in which pH adjustment is performed by adding a pH adjuster to the first solution.

<15> The method described in <13> or <14> in which a pH of the first solution after the pH adjustment is suitably 3.0 or more, more suitably 3.3 or more, and much more suitably 3.5, and is suitably 5.5 or less, more suitably 5.3 or less, and much more suitably 5.0 or less.

<16> The method described in any one of <1> to <15> in which the first solution is subjected to filtration.

<17> The method described in <16> in which the first solution is caused to circulate in a circulation pipe provided with a filter so that circulating filtration is performed.

<18> The method described in <16> in which the first solution is distributed in a filtration pipe provided with a filter so that one-pass filtration is performed.

<19> The method described in <17> or <18> in which an aperture of a filter medium disposed in the filter is suitably 0.1 μm or more, more suitably 0.5 μm or more, and much more suitably 1.0 μm or more, and is suitably 5.0 μm or less, more suitably 2.0 μm or less, and much more suitably 1.5 μm or less.

<20> The method described in any one of <1> to <19> in which in the step 2, an oxygen concentration in the tank A is reduced.

<21> The method described in <20> in which the oxygen concentration in the tank A is reduced by supplying an inert gas to the tank A.

<22> The method described in <21> in which supply of the inert gas to the tank A is continuously performed in an operation in the step 2.

<23> The method described in any one of <20> to <22> in which an oxygen concentration of a gaseous phase in the tank A is suitably 1.0% by volume or less, and more suitably 0% by volume.

<24> The method described in any one of <1> to <23> in which the extraction solvent includes an organic solvent whose octanol/water distribution coefficient is 0 or more and 4.0 or less.

<25> The method described in any one of <1> to <24> in which the extraction solvent includes an organic solvent whose octanol/water distribution coefficient is suitably 0 or more and 1.5 or less, and more suitably 0 or more and less than 0.90.

<26> The method described in any one of <1> to <25> in which the extraction solvent includes one or more of ethyl acetate, diethyl ether, methyl isobutyl ketone, dichloromethane, and cyclohexane.

<27> The method described in <25> or <26> in which the extraction solvent includes ethyl acetate.

<28> The method described in any one of <1> to <27> in which an amount of addition of the extraction solvent to the first solution with respect to a volume of the first solution at the end of reaction is suitably 20% by volume or more, more suitably 30% by volume or more, and much more suitably 50% by volume or more, and is suitably 400% by volume or less, more suitably 200% by volume or less, and much more suitably 100% by volume or less.

<29> The method described in any one of <1> to <28> in which the first solution is agitated after the first solution is mixed with the extraction solvent, or while the extraction solvent is added to the first solution.

<30> The method described in <29> in which an agitation time (extraction time) of the first solution is suitably 10 minutes or more, more suitably 15 minutes or more, and much more suitably 20 minutes or more, and is suitably 120 minutes or less, more suitably 90 minutes or less, and much more suitably 60 minutes or less.

<31> The method described in any one of <1> to <30> in which cleaning of the second solution is performed with wash water.

<32> The method described in <31> in which the cleaning of the second solution with the wash water is performed such that the wash water is brought into sufficient contact with the second solution by adding the wash water while the second solution is agitated, and then, phase separation into an oil phase of the second solution and a water phase of the wash water is performed.

<33> The method described in <32> in which an amount of addition of the wash water to the second solution with respect to a volume of the second solution is suitably 10% by volume or more, more suitably 20% by volume or more, and much more suitably 30% by volume or more, and is suitably 100% by volume or less, more suitably 80% by volume or less, and much more suitably 50% by volume or less.

<34> The method described in any one of <31> to <33> in which a cleaning time of the second solution with the wash water is suitably 30 minutes or more, more suitably 45 minutes or more, and much more suitably 60 minutes or more, and is suitably 120 minutes or less, more suitably 105 minutes or less, and much more suitably 90 minutes or less.

<35> The method described in any one of <31> to <34> in which the wash water includes polybasic acid salt.

<36> The method described in <35> in which the polybasic acid salt includes one or more of potassium salt of phosphoric acid, potassium salt of citric acid, potassium salt of carbonic acid, sodium salt of phosphoric acid, sodium salt of citric acid, and sodium salt of carbonic acid.

<37> The method described in any one of <1> to <36> in which the tank B is another solution tank different from the tank A.

<38> The method described in <37> in which the tank B is a tank an inside of which is cleaned.

<39> The method described in any one of <1> to <36> in which the tank B is the tank A an inside of which is cleaned after the second solution obtained in the step 2 is discharged.

<40> The method described in <38> or <39> in which cleaning of the inside of the tank B is performed with water.

<41> The method described in any one of <1> to <40> in which in the step 3, an oxygen concentration in the tank B is reduced.

<42> The method described in <41> in which the oxygen concentration in the tank B is reduced by supplying an inert gas into the tank B.

<43> The method described in <42> in which supply of the inert gas to the tank B is continuously performed during an operation of the step 3.

<44> The method described in any one of <41> to <43> in which an oxygen concentration of a gaseous phase in the tank B is suitably 1.0% by volume or less, and more suitably 0% by volume.

<45> The method described in any one of <1> to <44> in which the water has a dissolved oxygen concentration of suitably 1.0 mg/L or less, and more suitably 0.5 mg/L or less.

<46> The method described in any one of <1> to <45> in which first addition of the water to the second solution is performed on the second solution after supply to the tank B.

<47> The method described in any one of <1> to <45> in which first addition of the water to the second solution is performed on the second solution that has been discharged from the tank A and has not yet been supplied to the tank B.

<48> The method described in any one of <1> to <47> in which an amount of addition of the water with respect to a volume of the second solution is suitably 50% by volume or more, more suitably 80% by volume or more, and much more suitably 100% by volume or more, and is suitably 150% by volume or less, more suitably 120% by volume or less, much more suitably 110% by volume or less.

<49> The method described in any one of <1> to <48> in which a liquid temperature in evaporating the extraction solvent is suitably 40° C. or more, more suitably 50° C. or more, and much more suitably 60° C. or more, and is suitably 90° C. or less, more suitably 85° C. or less, and much more suitably 80° C. or less.

<50> The method described in any one of <1> to <49> in which a pressure in evaporating the extraction solvent for the first time is suitably an atmospheric pressure (101.325 kPa (abs)) or less, more suitably 90 kPa (abs) or less, and much more suitably 80 kPa (abs) or less.

<51> The method described in any one of <1> to <50> in which addition of the water to the second solution and evaporation of the extraction solvent are performed a plurality of times.

<52> The method described in <51> in which addition of the water to the second solution and evaporation of the extraction solvent are performed twice or more and four times or less.

<53> The method described in <51> or <52> in which a pressure in evaporating the extraction solvent at second and subsequent times is suitably 80 kPa (abs) or less, more suitably 40 kPa (abs) or less, and much more suitably 10 kPa (abs) or less.

<54> The method described in any one of <1> to <53> in which after addition of the water and evaporation of the extraction solvent, water and a water-soluble solvent are added in liquid remaining in the tank B to perform concentration adjustment so that the third solution is thereby obtained.

<55> The method described in <54> in which the water-soluble solvent includes ethanol.

<56> The method described in any one of <1> to <55> in which a content of the DHIs in the third solution is suitably 0.3% by mass or more, more suitably 0.5% by mass or more, and much more suitably 1.0% by mass or more.

<57> The method described in any one of <1> to <56> in which a total cyan concentration in the third solution is suitably 10 mg/L or less, more suitably 5 mg/L or less, much more suitably 1 mg/L or less, and much more suitably 0.5 mg/L or less.

<58> The method described in any one of <1> to <57> in which a content of cyan with respect to one part by mass of the DHIs in the third solution is suitably 10 mg/L or less, more suitably 5 mg/L or less, and much more suitably 1 mg/L or less.

<59> The method described in any one of <1> to <58> in which a content of an organic solvent in the third solution is suitably 1.5% by mass or less, more suitably 1.0% by mass or less, and much more suitably 0.5% by mass or less.

<60> The method described in any one of <1> to <59> in which the second solution is condensed before addition of the water and evaporation of the extraction solvent.

<61> The method described in <60> in which in an condensation operation of the second solution, the extraction solvent is evaporated from the second solution obtained in the step 2 in the tank A, and then, the condensed second solution is discharged from the tank A and supplied to and stored in the tank B.

<62> The method described in <60> in which in a condensation operation of the second solution, the second solution obtained in the step 2 is discharged from the tank A and supplied to and stored in the tank B, and then, in the tank B, the extraction solvent is evaporated so that the second solution is thereby condensed.

<63> The method described in <60> in which in a condensation operation of the second solution, the second solution obtained in the step 2 is discharged from the tank A and supplied to another solution tank, and the extraction solvent is evaporated for condensation, and then the second solution is discharged from the solution tank, and the condensed second solution is supplied to and stored in the tank B.

EXAMPLES (Production of DHI Aqueous Solution)

DHI aqueous solutions were produced according to first through fourth examples and first and second comparative examples. The production was performed under a nitrogen atmosphere. The results of the production are also shown in Table 1.

First Example

As a tank A, a reaction tank provided with an agitator including an anchor impeller and a temperature-adjusting jacket, having a capacity of 300 L, and made of SUS was used. A nitrogen gas was continuously supplied to the tank A, and water into which a nitrogen gas was blown so that the dissolved oxygen concentration was 1.0 mg/L or less was poured in the tank A. While water was agitated in the tank A by starting the agitator, DOPA was placed and dissolved, thereby preparing 175 L of a DOPA aqueous solution having a concentration of 0.33% by mass. At this time, the liquid temperature of the DOPA aqueous solution was adjusted to 35° C. by heating with the jacket.

In addition, water was poured in an oxidizing agent tank provided with an agitator. While water was agitated in the oxidizing agent tank by starting the agitator, potassium hexacyanoferrate(III) and potassium hydrogencarbonate were placed and dissolved, thereby preparing 25.2 L of a potassium hexacyanoferrate(III) aqueous solution (oxidizing agent solution) having a concentration of 16.8% by mass. The content of potassium hexacyanoferrate(III) in this potassium hexacyanoferrate(III) aqueous solution was 4.0 equivalents with respect to the mole number of DOPA in the DOPA aqueous solution. The content of potassium hydrogencarbonate of a base agent in the potassium hexacyanoferrate(III) aqueous solution was 6.0 equivalents with respect to the mole number of DOPA in the DOPA aqueous solution.

Next, while the DOPA aqueous solution was agitated in the tank A, the potassium hexacyanoferrate(III) aqueous solution in the oxidizing agent tank was dropped in the tank A for 10 minutes, and aging was performed for four hours from the start of dropping so that DOPA was oxidized, thereby obtaining a DHI aqueous solution as a first solution. During this process, the liquid temperature of the reaction solution in the tank A was maintained at 35° C.

Thereafter, while the first solution in the tank A was agitated, a phosphoric acid aqueous solution having a dissolved oxygen concentration of 1.0 mg/L or less and a concentration of 10% by mass was added as a pH adjuster to the tank A so that the pH was adjusted to 4.7.

Subsequently, the first solution subjected to the pH adjustment in the tank A was filtered by circulating filtration. At this time, a filter medium of a filter having an aperture of 1.2 μm was used.

Then, while the first solution of the filtrate subjected to the circulating filtration in the tank A was agitated, 100 L of ethyl acetate was added as an extraction solvent to the tank A, and DHI extraction in the extraction solvent of ethyl acetate was performed for 20 minutes, and then, a lower layer of a water phase after phase separation was discharged, thereby obtaining a DHI ethyl acetate solution as a second solution. The amount of addition of the ethyl acetate was 50% by volume with respect to the volume of the first solution at the end of the reaction.

Thereafter, while the second solution was agitated in the tank A, wash water in which dipotassium hydrogen phosphate and potassium dihydrogen phosphate were dissolved in water (salt concentration: 8.33% by mass, dipotassium hydrogen phosphate/potassium dihydrogen phosphate (mass ratio)=5.12) was added to the tank A, and cleaning of the second solution was performed for 90 minutes, and then, a lower layer of a water phase after phase separation was discharged. At this time, the amount of addition of wash water was 40% by volume with respect to the volume of the second solution.

Subsequently, while the cleaned second solution in the tank A was agitated, the liquid temperature of the second solution was heated to 80° C., and the pressure in the tank was reduced to 90 kPa (abs), and ethyl acetate in the extraction solvent was evaporated, thereby condensing the second solution.

Then, the condensed second solution was discharged from the tank A and transferred to a tank B that is a solution tank different from the tank A. The tank B was a reaction tank provided with an agitator including an anchor impeller and a temperature-adjusting jacket and having a capacity of 10 L, and was prepared by washing the inside of the tank with water and blowing a nitrogen gas into the tank so that the oxygen concentration in the tank was 0% by volume. The tank B was made of SUS.

Thereafter, while the condensed second solution was agitated in the tank B, water is added to the tank B, and then, the liquid temperature of the resulting mixture was heated to 80° C. and the pressure in the tank was reduced to 80 kPa (abs) so that ethyl acetate in the extraction solvent was evaporated, thereby performing first solvent displacement. At this time, the amount of addition of water was 100% by volume with respect to the volume of the second solution.

Subsequently, while liquid remaining in the tank B was agitated, water was added to the tank B, and then, the liquid temperature of the resulting mixture was heated to 80° C., and the pressure in the tank was reduced to 25 kPa (abs) so that ethyl acetate in the extraction solvent was evaporated, thereby performing second solvent displacement. At this time, the amount of addition of water was 100% by volume with respect to the volume of water remaining in the tank B. Third solvent displacement was also performed by a similar operation.

With the third solvent displacement, while liquid remaining in the tank B was agitated, water and ethanol were added to the tank B for concentration adjustment, thereby obtaining, as a third solution, a DHI aqueous solution having a DHI content of 1.1% by mass. The obtained DHI aqueous solution was used as a first example.

Second Example

As a tank A, a reaction tank provided with an agitator including a tilt paddle impeller and a temperature-adjusting jacket, having a capacity of 8 m$^3$, and made of SUS was used. As a tank B, a reaction tank provided with an agitator including a tilt paddle impeller and made of SUS and a temperature-adjusting jacket, having a capacity of 6 m$^3$ was used. In the tank A, 4.61 m$^3$ of a DOPA aqueous solution having a concentration of 0.33% by mass was prepared. In the oxidizing agent tank, 0.61 m$^3$ of a potassium hexacyanoferrate(III) aqueous solution having a concentration of 16.8% by mass was prepared. In addition, 2.65 m$^3$ of ethyl acetate of an extraction solvent was used. Except for these processes, an operation similar to that of the first example was performed, thereby obtaining a DHI aqueous solution as a second example.

Third Example

As a tank A, a reaction tank provided with an agitator including an anchor impeller and a temperature-adjusting jacket, having a capacity of 30 L, and made of polytetrafluoroethylene was used. In the tank A, 17.9 L of a DOPA aqueous solution having a concentration of 0.33% by mass was prepared. In an oxidizing agent tank, 2.38 L of a potassium hexacyanoferrate(III) aqueous solution having a concentration of 16.8% by mass was prepared. In addition, 10.0 L of ethyl acetate of an extraction solvent was used. A second solution discharged from the tank A was temporarily supplied to and stored in a sealable glass container in which the oxygen concentration was reduced to 0% by volume with a nitrogen gas beforehand and having a capacity of 1 L. After the tank A from which the second solution was discharged was cleaned, the second solution was returned from the glass container to the tank A, that is, the tank A whose inside was cleaned was used as the tank B. Except for these processes, an operation similar to that of the first example was performed, thereby obtaining a DHI aqueous solution as a third example. The cleaning of the inside of the tank A was performed by pouring water in the tank A from which the second solution was discharged, agitating water for 60 minutes, and then discharging water. The oxygen concentration in the tank A after the cleaning was 0% by volume.

Fourth Example

As a tank A, a reaction tank provided with an agitator including an anchor impeller and a temperature-adjusting jacket, having a capacity of 4 $m^3$, and made of SUS was used. As a tank for storing a second solution, a SUS open drum having an oxygen concentration previously reduced to 0% by volume by using a nitrogen gas, having a capacity of 200 L, allowing a nitrogen gas to be distributed therein was used as a tank for storing a second solution. In the tank A, 2.36 $m^3$ of a DOPA aqueous solution having a concentration of 0.33% by mass was prepared. In an oxidizing agent tank, 0.31 $m^3$ of a potassium hexacyanoferrate(III) aqueous solution having a concentration of 16.7% by mass was prepared. In addition, 1.33 $m^3$ of ethyl acetate of an extraction solvent was used. Except for these processes, an operation similar to that of the third example was performed, thereby obtaining a DHI aqueous solution as a fourth example.

First Comparative Example

In a tank A, 17.8 L of a DOPA aqueous solution having a concentration of 0.34% by mass was prepared. In an oxidizing agent tank, 2.38 L of a potassium hexacyanoferrate (III) aqueous solution having a concentration of 16.8% by mass was prepared. In addition, 10.2 L of ethyl acetate of an extraction solvent was used. The tank A was used solely without using a tank B. Except for these processes, an operation similar to that of the first example was performed, thereby obtaining a DHI aqueous solution as a first comparative example.

Second Comparative Example

In a tank A, 175 L of a DOPA aqueous solution having a concentration of 0.33% by mass was prepared. In an oxidizing agent tank, 25.2 L of a potassium hexacyanoferrate (III) aqueous solution having a concentration of 16.8% by mass was prepared. In addition, 100 L of ethyl acetate of an extraction solvent was used. The tank A was used solely without using a tank B. Except for these processes, an operation similar to that of the first example was performed, thereby obtaining a DHI aqueous solution as a second comparative example.

TABLE 1

|  |  | Example | | | | Comparative Example | |
|---|---|---|---|---|---|---|---|
|  |  | 1 | 2 | 3 | 4 | 1 | 2 |
| Tank A | capacity | 300 L | 8 $m^3$ | 30 L | 4 $m^3$ | 30 L | 300 L |
| Tank B |  | — | 10 L | 6 $m^3$ | Tank A | Tank A | — | — |
| DOPA aqueous solution | concentration (% by mass) | 0.33 | 0.33 | 0.33 | 0.33 | 0.34 | 0.33 |
|  | pouring amount | 175 L | 4.61 $m^3$ | 17.9 L | 2.36 $m^3$ | 17.8 L | 175 L |
| potassium hexacyano-ferrate(III) aqueous solution | concentration (% by mass) | 16.8 | 16.8 | 16.8 | 16.7 | 16.8 | 16.8 |
|  | addition amount | 25.2 L | 0.61 $m^3$ | 2.38 L | 0.31 $m^3$ | 2.38 L | 25.2 L |
|  | DOPA equivalent (eq.) | 4.0 | 4.0 | 4.0 | 4.0 | 4.0 | 4.0 |
| extraction solvent (ethyl acetate) | addition amount | 100 L | 2.65 $m^3$ | 10.0 L | 1.33 $m^3$ | 10.2 L | 100 L |
|  | volume to first reaction solution (at reaction end) (% by volume) | 50 | 50 | 50 | 50 | 50 | 50 |
| DHI aqueous solution | total cyan concentration (mg/L) | less than 0.1 | less than 0.1 | 0.4 | less than 0.1 | 31.2 | 180 |

(Test Method and Result)

For the DHI aqueous solutions of the first through fourth examples and the first and second comparative examples, total cyan concentrations were measured by a picric acid method using a water quality measuring reagent set No. 46 all cyan produced by KYORISTU CHEMICAL-CHECK Lab., Corp. (R-1 reagent: acidic powder, R-2 reagent: alkaline powder) and a Digital Pack Test Multi SP. Specifically, a measurement operation was performed as follows.

One R-2 reagent was placed in a receiver of a distillation reactor, and then, a rod-equipped inner tube was fitted onto the distillation reactor from above. Then, 1 mL of ion-exchanged water measured by a dropper was added to the receiver so that the R-2 reagent was coated therewith, and the receiver was covered with a cap.

Next, 1.0 g of a DHI aqueous solution was weighed in a volumetric flask and adjusted up to 50 mL by diluting, and the resulting test water was placed in the flask. Then, immediately after one spoon of a R-1 reagent was added to the flask, the receiver was fixed to the flask with a spring.

Then, the distillation reactor was placed on an electric heating regulator and heated. When the test water was boiled, the voltage applied to the electric heating regulator was reduced and distillation was performed for 15 minutes. Thereafter, the electric heating regulator was turned off for cooling.

Thereafter, after it was confirmed that the regulator was cooled, the cap was taken off and the inner tube was removed. Liquid adhering to the inner tube was washed into the receiver with a small amount of ion-exchanged water, and the receiver was detached from the flask. Then, the liquid was diluted with ion-exchanged water to 25 mL and the resulting mixture was sufficiently mixed, thereby obtaining a measurement solution.

Then, the entire amount of the obtained measurement solution was transferred to a No. 6 screw tube, and a total cyan concentration was measured by using a Digital Pack Test Multi SP.

Table 1 shows test results. As shown in Table 1, in the first through fourth examples in which DHI was extracted in the tank A, and after the second solution was discharged from the tank A, the second solution was supplied to the tank B whose inside was cleaned, and solvent displacement was performed in this tank B, the total cyan concentrations were very low. On the other hand, in the first and second comparative examples in which solvent displacement was performed in the tank A where DHI was extracted, the total cyan concentrations were very high.

With a comparison between the first example and the second comparative example and a comparison between the third example and the first comparative example that are different only in the presence of transfer of the second solution, in the first and third examples in which the second solution was transferred, in the process in which the second solution was discharged from the tank A and supplied to the tank B, and then in this tank B, the second solution was subjected to solvent displacement to obtain the third solution, there was no cause of supply of cyanide from the outside, and thus, an increase in the content of cyanide is theoretically impossible. On the other hand, in the first and second comparative examples in which the second solution was not transferred, cyanide was supplied from the outside in the process of obtaining the third solution from the second solution, and the content of cyanide increased, and a supply source of cyanide is supposed to be the tank A.

INDUSTRIAL APPLICABILITY

The present invention is useful for a technical field of a method for producing DHIs.

DESCRIPTION OF REFERENCE CHARACTERS

L1 first solution
L2 second solution
L3 third solution
W water
10 reaction apparatus
11 reaction tank
12 oxidizing agent tank
13 oxidizing agent supply pipe
14 discharge pipe
151, 152 agitator
151a, 152a agitating impeller
16 jacket
171, 172 filter
181 circulation pipe
182 filtration pipe
19 filtrate tank
20A tank A
20B tank B
21 solution tank

The invention claimed is:

1. A method for producing dihydroxyindoles, comprising:
   a step 1 of obtaining an aqueous first solution including dihydroxyindoles obtained by causing at least a material selected from the group consisting of 3-(3,4-dihydroxyphenyl)alanine and a derivative of 3-(3,4-dihydroxyphenyl)alanine to react with hexacyanoferrate (III);
   a step 2 of obtaining an oleaginous second solution in which the dihydroxyindoles are extracted in an extraction solvent by mixing the first solution obtained in the step 1 with the extraction solvent; and
   a step 3 of obtaining an aqueous third solution by evaporating the extraction solvent from a mixture of the second solution obtained in the step 2 and water, wherein
   the dihydroxyindoles are extracted in a tank A in the step 2, the second solution is discharged from the tank A, the second solution is supplied to a tank B, and then the step 3 is performed in the tank B.

2. The method according to claim 1, wherein the tank B is a solution tank different from the tank A.

3. The method according to claim 2, wherein the tank B is a solution tank in which inside of the solution tank is cleaned.

4. The method according to claim 1, wherein the tank B is the tank A in which inside of the tank A is cleaned after the second solution obtained in the step 2 is discharged.

5. The method according to claim 3, wherein inside of the tank B is cleaned with water.

6. The method according to claim 1, wherein the extraction solvent includes an organic solvent whose octanol/water distribution coefficient is less than 0.90.

7. The method according to claim 6, wherein the extraction solvent includes ethyl acetate.

8. The method according to claim 1, wherein the tank A is made of stainless steel.

9. The method according to claim 1, wherein the tank B is made of stainless steel.

10. The method according to claim 1, wherein first addition of water to the second solution is performed on the second solution that has been discharged from the tank A and has not yet been supplied to the tank B.

11. The method according to claim 1, wherein an amount of addition of the water is 50% by volume or more and 150% by volume or less with respect to a volume of the second solution.

12. The method according to claim 1, wherein a liquid temperature in evaporating the extraction solvent is 40° C. or more and 90° C. or less.

13. The method according to claim 1, wherein addition of water to the second solution and evaporation of the extraction solvent are performed a plurality of times.

14. The method according to claim 1, wherein the third solution is obtained by adding water and a water-soluble solvent to liquid remaining in the tank B after addition of the water and evaporation of the extraction solvent for concentration adjustment.

15. The method according to claim 14, wherein the water-soluble solvent includes ethanol.

* * * * *